United States Patent
Koehler et al.

(10) Patent No.: US 10,314,556 B2
(45) Date of Patent: Jun. 11, 2019

(54) OPTIMAL ENERGY WEIGHTING OF DARK FIELD SIGNAL IN DIFFERENTIAL PHASE CONTRAST X-RAY IMAGING

(71) Applicant: KONINKLIJKE PHILIPS N.V., Eindhoven (NL)

(72) Inventors: Thomas Koehler, Norderstedt (DE); Ewald Roessl, Henstedt-Ulzburg (DE); Gerhard Martens, Henstedt-Ulzburg (DE); Heiner Daerr, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/312,693

(22) PCT Filed: Apr. 25, 2016

(86) PCT No.: PCT/EP2016/059114
§ 371 (c)(1),
(2) Date: Nov. 21, 2016

(87) PCT Pub. No.: WO2016/177588
PCT Pub. Date: Nov. 10, 2016

(65) Prior Publication Data
US 2018/0228455 A1    Aug. 16, 2018

(30) Foreign Application Priority Data
May 6, 2015    (EP) .................................... 15166504

(51) Int. Cl.
*A61B 6/03* (2006.01)
*A61B 6/00* (2006.01)
(Continued)

(52) U.S. Cl.
CPC .............. *A61B 6/484* (2013.01); *A61B 6/032* (2013.01); *A61B 6/405* (2013.01); *A61B 6/4035* (2013.01);
(Continued)

(58) Field of Classification Search
CPC ..... A61B 6/032; A61B 6/4035; A61B 6/4208; A61B 6/4233; A61B 6/4241; A61B 6/4291; A61B 6/482; A61B 6/484
(Continued)

(56) References Cited

U.S. PATENT DOCUMENTS

| | | | | |
|---|---|---|---|---|
| 5,812,629 A | * | 9/1998 | Clauser .................. | A61B 6/032 378/37 |
| 6,052,433 A | * | 4/2000 | Chao ........................ | A61B 6/06 378/147 |

(Continued)

FOREIGN PATENT DOCUMENTS

WO    2014/002026    1/2014

OTHER PUBLICATIONS

P M Shikhaliev, "Projection x-ray imaging with photon energy weighting: experimental evaluation with a prototype detector", Physics in Medicine and Biology 54(16):4971-4992 (2009).
(Continued)

*Primary Examiner* — Allen C. Ho
(74) *Attorney, Agent, or Firm* — Larry Liberchuk

(57) ABSTRACT

Apparatus and related method for dark-field imaging. The apparatus operates on projective intensities detected at a detector in different energy channels. An energy weighting is used to improve the signal to noise ratio. The model operates in a logarithmic domain.

14 Claims, 4 Drawing Sheets

(51) Int. Cl.
  *G01N 23/04* (2018.01)
  *G01N 23/041* (2018.01)
(52) U.S. Cl.
  CPC .......... *A61B 6/4208* (2013.01); *A61B 6/4233* (2013.01); *A61B 6/4241* (2013.01); *A61B 6/4291* (2013.01); *A61B 6/482* (2013.01); *A61B 6/5205* (2013.01); *G01N 23/04* (2013.01); *G01N 23/041* (2018.02)
(58) Field of Classification Search
  USPC .......................... 378/19, 36, 62; 250/370.09
  See application file for complete search history.

(56) References Cited

U.S. PATENT DOCUMENTS

| | | | | |
|---|---|---|---|---|
| 8,121,249 | B2* | 2/2012 | Wang | A61B 6/032 378/6 |
| 9,001,967 | B2* | 4/2015 | Baturin | A61B 6/484 378/156 |
| 9,036,773 | B2* | 5/2015 | David | A61B 6/4035 378/36 |
| 9,357,975 | B2* | 6/2016 | Baturin | G01N 23/20075 |
| 9,408,585 | B2* | 8/2016 | Oh | A61B 6/484 |
| 9,439,615 | B2* | 9/2016 | Stampanoni | A61B 6/484 |
| 9,494,534 | B2* | 11/2016 | Baturin | G01N 23/20075 |
| 9,700,267 | B2* | 7/2017 | Baturin | A61B 6/587 |
| 9,700,275 | B2* | 7/2017 | Stampanoni | A61B 6/483 |
| 9,724,063 | B2* | 8/2017 | Baturin | A61B 6/5205 |
| 9,801,600 | B2* | 10/2017 | Wang | A61B 6/484 |
| 9,907,524 | B2* | 3/2018 | Baturin | A61B 6/484 |
| 9,959,640 | B2* | 5/2018 | Koehler | G06T 11/60 |
| 10,096,098 | B2* | 10/2018 | Baturin | G01T 1/164 |
| 2014/0185746 | A1 | 7/2014 | Baturin | |
| 2014/0270064 | A1 | 9/2014 | Oh | |

OTHER PUBLICATIONS

G Pelzer et al, "Grating-based x-ray phase-contrast imaging with a multi energy-channel photon-counting pixel detector", Optics Express, Nov. 4, 2013, vol. 21, No. 22, pp. 25677-25684.

G Pelzer et al "Energy weighted x-ray dark-field Imaging", Optics Express, Oct. 6, 2014, vol. 22, No. 20, pp. 24507-24515.

F M Epple et al, "Unwrapping differential X-ray phase contrast images through phase estimation from multiple energy data", Optics Express, Dec. 2, 2013, vol. 21, No. 24.

F. Pfeiffer et al in "Phase retrieval and differential phase-contrast imaging with low-brilliance X-ray sources," Nature Phys. Lett. 2, 258-261 (2006).

M Bech et al in "Quantitative X-ray dark-field computed tomography", Phys. Med. Biol. 55 (2010) 5529-5539.

A. Guinier, "X-Ray Diffraction", Dover Publications, Inc, New York, (1994), Chapter 10.

Weber et al., "Noise in x-ray grating based phase-contrast imaging", Medical Physics 38(7):4133-4140 (2011).

Wunderlich, "Image covariance and lesion detectability in direct fan-beam x-ray computed tomography", Physics in Medicine and Biology, 53:2471-2493 (2008).

Gudbarjartsson et al, "The Rician Distribution for Noisy MRI Data", MRM 34:910-914 (1995).

Henkelman, "Measurement of signal intensities in the presence of noise in MR images", Medical Physics 12:232-233 (1985), Erratum in 13:544 (1986).

Revol et al., "Orientation-selective X-ray dark field imaging of ordered systems", Journal of Applied Physics 112:114903 (2012).

Yashiro et al., "On the origin of visibility contrast in x-ray Talbot interferometry", Optics Express 18(6):16890 (2010).

Wang et al., "Non-invasive classification of microcalcifications with phase-contrast X-ray mammography", Nature Communications 5:3797 (2014).

Michel et al., "On a dark-field signal generated by micrometer-sized calcifications in phase-contrast mammography", Physics in Medicine and Biology, 58: 2713-2732 (2013).

Hauser et al., "A Study on Mastectomy Samples to Evaluate Breast Imaging Quality and Potential Clinical Relevance of Differential Phase Contrast Mammography", Investigative Radiology, 49(3):131-137 (2013).

Stutman et al., "Talbot phase-contrast x-ray imaging for the small joints of the hand", Physics in Medicine and Biology, 56(17):5697-5720 (2011).

Koehler, et al., "Non-Scatter Contributions to the Dark-Field Signal in Differential Phase Contrast Imaging", American Institute of Physics, 2012.

Malecki et al., "Quantitative wave-optical numerical analysis of the dark-field signal in grating-based X-ray Interferometry", EPL 99, 48001 (2012).

Pelzer, et al., "Energy-resolved interferometric X-ray imaging", Medical Imaging 2013.

* cited by examiner

OPTIMAL ENERGY WEIGHTING OF DARK FIELD SIGNAL IN DIFFERENTIAL PHASE CONTRAST X-RAY IMAGING

CROSS REFERENCE TO RELATED APPLICATIONS

This application is the U.S. National Phase application under 35 U.S.C. § 371 of International Application No. PCT/EP2016/059114, filed Apr. 25, 2016, published as WO 2016/177588 on Nov. 10, 2016, which claims the benefit of European Patent Application Number 15166504.9 filed May 6, 2015. These applications are hereby incorporated by reference herein.

FIELD OF THE INVENTION

The invention relates to a signal processing apparatus, to an imaging system, to a signal processing method, to a computer program element and to a computer readable medium.

BACKGROUND OF THE INVENTION

Differential phase contrast imaging using a Talbot-Lau-type interferometer has been studied extensively over the last few years with respect to the potential benefit for diagnostic imaging, in particular in the area of orthopedics and mammography. This imaging method provides in addition to the conventional image of X-ray attenuation two further images, namely the differential phase contrast image, reflecting information of the electron density within the imaged object, and the dark field image, where the contrasts are created by small angle scattering. In particular the dark field signal/image gained considerable interest lately, since there is evidence that micro-calcifications show up at a very early stage in this image, even before the calcifications are large enough to become visible in the attenuation contrast images, and there is evidence that the dark field signal can be used to classify different types of calcifications.

Another forthcoming technology in medical X-ray imaging is the use of energy resolving photon counting detectors. In the area of attenuation contrast imaging, the use of the detector type allows to discriminate between attenuation of the X-ray due to the photo-electric effect and Compton scattering. It further allows providing an attenuation contrast image with improved contrast to noise ratio by means of so-called energy weighting [P M Shikhaliev, "Projection x-ray imaging with photon energy weighting: experimental evaluation with a prototype detector", Physics in Medicine and Biology 54(16):4971-4992 (2009)]. A similar concept has been used in the area of differential phase contrast imaging [G Pelzer et al, "Grating-based x-ray phase-contrast imaging with a multi energy-channel photon-counting pixel detector", OPTICS EXPRESS, 4 Nov. 2013, Vol 21, No 22, pp 25677-25684] and dark-field imaging [G Pelzer et al "Energy weighted x-ray dark-field Imaging", OPTICS EXPRESS, 6 Oct. 2014, Vol. 22, No. 20, pp 24507-24515], where energy weighting may also improve the signal to noise ratio.

SUMMARY OF THE INVENTION

There may be a need for an alternative dark field imaging apparatus and method.

The object of the present invention is solved by the subject matter of the independent claims where further embodiments are incorporated in the dependent claims. It should be noted that the following described aspect of the invention equally apply to the imaging system, to the signal processing method, to the computer program element, and to the computer readable medium.

According to a first aspect of the invention there is provided a signal processing apparatus, comprising:

an input port for receiving, in different energy channels, respective dark-field signal data, the dark-field signal data corresponding to signals detected, in the different energy channels, at a detector after exposure to X-ray radiation from an X-ray source;

log unit configured to logarithmize the dark-field signal data to obtain log-dark-field-signal data;

an optional linear transformer configured to transform the log-dark-field-signal data;

a signal integrator configured to integrate the transformed log-dark-field signal data or the log-dark-field-signal data of the at least two energy channels into an energy weighted log-dark-field signal by using energy weights corresponding to the at least two energy channels; and an output port configured to output said energy weighted log-dark-field signal.

The dark-field signal relates to X-ray radiation scattering (small angle scattering that is) caused by an imaged object after exposing same to X-ray radiation.

The dark field signal data per energy channel can be obtained either directly by suitable direct dark-field imaging techniques where it is ensured that the signals detected by the detector can be attributed mostly to small angle scattering. Alternatively, a set-up such as an interferometer can be used where the dark field signals are indirectly measured. More particularly, if indirect dark-field imaging is used, the apparatus comprises in one embodiment a dark-field signal extractor configured to extract, for at least two of said channels, the respective dark-field signal data from previously obtained intensity data. The intensity data may be derived from projection data detected, in the different energy channels, at the detector after exposure to X-ray radiation from an X-ray source.

The intensities are measured on projection data. More particularly, the "projective" intensities are detected preferably at a 2D detector that operates to spatially resolved the intensities in the two spatial directions perpendicular to the X-ray flux, hence the qualifier "projective" intensities.

According to one embodiment, the intensities form an interference pattern caused by interaction of the X-ray wave with the object to be imaged and with the technical set-up arranged between X-ray source and the detector. As mentioned, in one embodiment the projective intensities are interferometric, that is, the set-up is a grating-based interferometer. However, other, non-grating based set-ups are likewise envisaged.

Advantageously, processing in the logarithmic domain has been found by Applicant to yield good results and this modelling approach appears to capture well the underlying multiplicative drivers in the dark-field signal domain.

The different energy channels can be implemented in different ways. In one embodiment the detector is of the energy resolving (e.g., photon-counting) type and the different energy channels correspond to different energy values of the energy resolving detector. In an alternative embodiment, the detector is of the energy integrating type and the different energy channels correspond to detector readings for X-ray exposures by the X-ray source at different voltage levels.

According to one embodiment, the weights include respective energy terms of the form $E^p$ with p<−2 or can be so expressed in other algebraic forms equivalent to this form. More particularly, according to one embodiment, −4≤p<−2. Yet more particularly, according to one embodiment p is about −3.

In an alternative embodiment, the weights include respective energy terms, at least one of them having an energy value as an exponent.

In other words it is proposed herein to employ, in one embodiment, a photon counting detector to perform energy weighting of the dark field signal using a logarithmic domain representation of data. In an embodiment, the dependence on energy E of the signal is modelled as $E^p$ (p<−2) which model Applicant found to provide for an excellent fit with experimental data.

According to one embodiment, the weights include respective energy terms of the form $$\frac{a}{E_i^2} * \left(1 - \exp\left(-b\left(\frac{E_0}{E_i^2}\right)^2\right)\right)$$

(or algebraic equivalents thereof), wherein a is an arbitrary constant, b is a constant that relates to an internal structure of an imaged object, $E_0$ is a design energy and $E_i$ are the different energy levels for the channels i.

According to one embodiment, the linear transformer is any one of: (i) a high or low-pass filter, (ii) a backward-projection operator which in one embodiment is a filtered backward projection operator. Put differently, the proposed system can be used in both, 2D projection imaging and in 3D CT reconstruction imaging. More particularly, the energy integrating step can be applied in projection domain (in which case no linear operator is required although a filter operation can still be performed herein if desired). In other words, the signal integration step is performed on the projection data. In case of a CT application, the above signal integration/energy weighting step can be performed in image space instead although even in CT one may still wish to first perform the energy weighting and then back-project later. In other words, the energy integrating/weighting step is either performed in projection domain or in image domain.

According to a second aspect, there is provided the signal processing method, comprising:
receiving, in different energy channels, respective dark-field signal data;
logarithmizing the dark-field signal data to obtain log-dark-field-signal data;
optionally, linearly transforming the log-dark-field-signal data;
integrating the log-dark-field signal data or the transformed log dark-field signal data of the at least two channels into an energy weighted log-dark-field signal by using energy weights corresponding to the at least two energy channels, and
outputting said energy weighted log-dark-field signal.

According to one embodiment, the method further comprises extracting, for at least two of said channel, from the projective intensity data, the respective dark-field signals data, the projective intensity data (previously) detected in the different energy channels at a detector after exposure of same to X-ray radiation from an X-ray source.

The present invention allows for useful application in a clinical environment such as a hospital. More specifically, the present invention is very suitable for application in imaging modalities such as mammography, diagnostic radiology, interventional radiology and computed tomography (CT) for the medical examination of patients. In addition, the presentation invention allows for useful application in an industrial environment. More specifically, the present invention is very suitable for application in non-destructive testing (e.g. analysis as to composition, structure and/or qualities of biological as well non-biological samples).

BRIEF DESCRIPTION OF THE DRAWINGS

Exemplary embodiments of the invention will now be described with reference to the following drawings wherein.

DETAILED DESCRIPTION OF EMBODIMENTS

Figure 1:
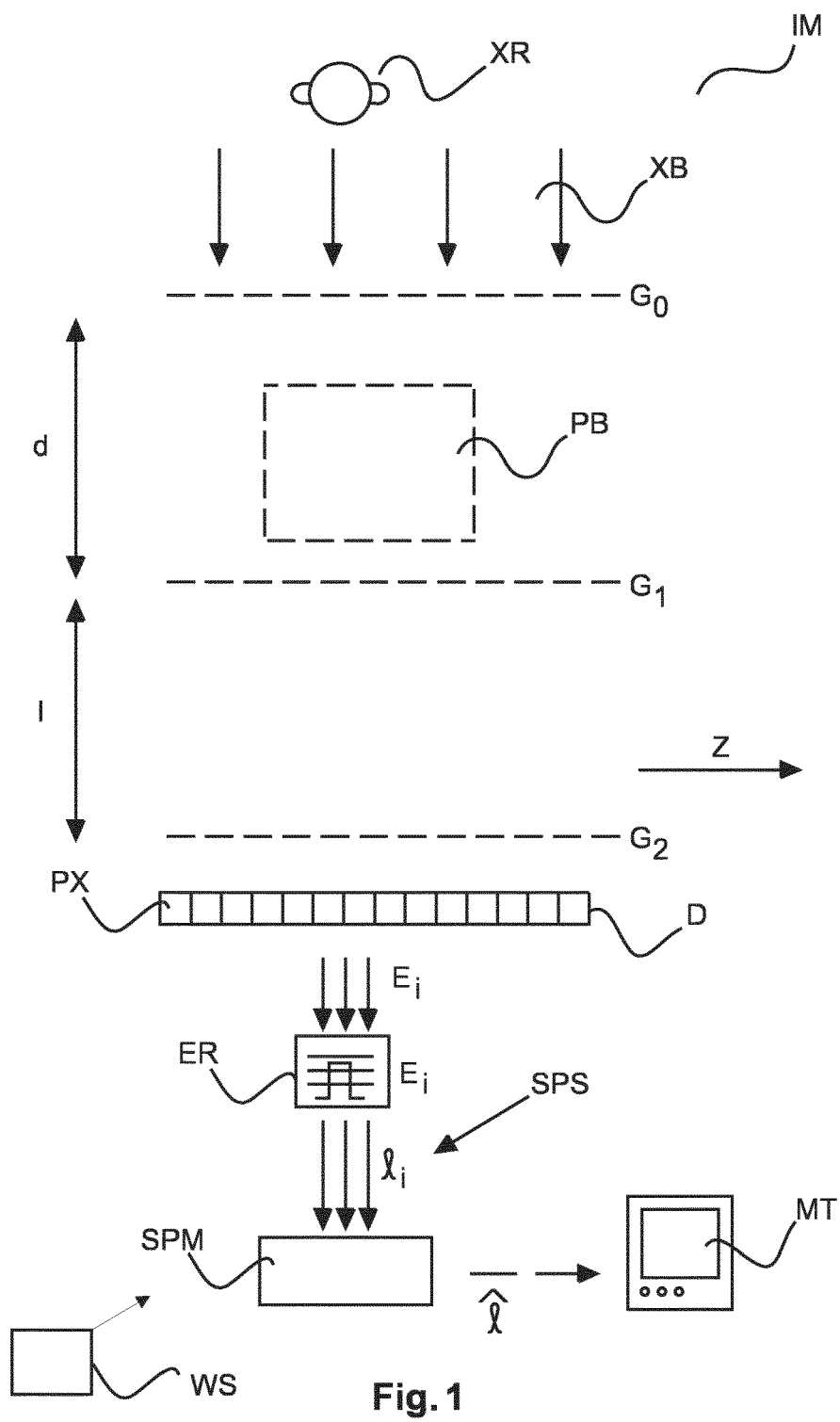
FIG. 1 shows an interferometric X-ray imaging apparatus with an energy resolving detector subsystem.

FIG. 1 shows a schematic block-diagram of an X-ray imaging system IM configured for energy-resolved phase contrast imaging, in particular dark filed imaging.

There is an X-ray source XR for generating X-ray radiation waves XB that, after passage through a specimen PB in an examination region, are detectable by detector pixels px of a detector D. An object support (not shown) such as a couch supports the specimen PB (such as a patient or an inanimate object, e.g. an item of baggage, etc) in the examination region.

The X-Ray imaging system IM is either a CT scanner for 3D imaging or may also be a simpler planar projection imager apparatus such as of the C-arm type. In one embodiment, the X-ray source is mounted on a rotatable gantry (not shown) to project the X-ray waves through the patient at any one or a plurality of desired projection directions. Simpler embodiments for 2D X ray projection imaging are also envisaged herein where the X-ray source is stationary.

As its basic components, the X-Ray imaging system IM includes an interferometric system component and, in one embodiment (but not necessarily all embodiments), an energy-resolving detector sub-system component.

Turning first in more detail to the interferometric system component and its operation, this component includes a sub-system of one, or two or more interferometric gratings, e.g. $G_0$-$G_2$. This sub-system of gratings affords the phase contrast imaging capability, in particular a differential phase contrast imaging, "DPCI", by suitably arranging the gratings between the X-ray source XR and the radiation sensitive detector D. The dark field signal (or small angle scattering signal) can be extracted in a context commonly referred to as grating based phase contrast imaging although other approaches such as analyzer-based imaging (diffraction-enhanced imaging (DEI) or propagation based imaging (refraction enhanced imaging)) are also envisaged herein in alternative embodiments. We therefore briefly summarize in the following aspects of phase contrast imaging relevant for the understanding of dark field imaging. However, this is not to exclude other embodiments, where the dark signal imaging is carried our directly without the phase contrast imaging set-up.

In an exemplary, non-limiting embodiment, grating-based setup, the interferometric equipment (which in one non-limiting embodiment is of the Talbot type or of the Talbot-Lau type) includes two $G_1$, $G_2$ (Talbot type) or more, preferably, three gratings $G_0$, $G_1$, and $G_2$ (Talbot-Lau type). A first attenuation grating $G_0$ at the X-ray source side has a period $p_0$ to generate at least partial spatial coherence of the X-ray radiation wave front emitted at the X-ray source XR.

A phase grating $G_1$ (having period $p_1$) is placed at distance d from the X-ray source and causes an interference pattern with period $p_2$ further downstream. Said interference pattern can be detected by detector D, either directly or by using a further so-called analyzer grating $G_2$. Now, when a sample PB (to be imaged) is introduced in the examination region between the X-ray source and the detector, the phase of the interference pattern is then shifted. This interference pattern shift $\Delta\varphi$ (as has been reported elsewhere, for instance in F M Epple et al, "Unwrapping differential X-ray phase contrast images through phase estimation from multiple energy data", OPTICS EXPRESS, 2 Dec. 2013, vol 21, No 24) is proportional to the gradient of the phase shift $\Delta\Phi$ due to the accumulated refraction along respective paths through the sample PB (hence the name DCPI). In other words, measuring the phase change of the interference allows extracting the shift (or gradient) of the phase that is caused by refraction in the sample PB.

Unfortunately the period of the interference pattern is typically too small to be directly spatially resolved which accordingly impedes a direct measurement of the phase of the pattern. The spatial resolution of most X-ray detectors would not allow this. Therefore in order to "sample" this interference pattern phase shift, a second attenuation grading G2 with the same period p2 as the interference pattern is normally placed at a distance 1 from grating G1 In some mono-grating embodiments, only one grating is used arranged at a suitable Talbot distance from the detector to ensure the interference pattern form at the detector plane.

To help extract the interference pattern's phase shift (and hence that of the phase gradient caused by the sample PB) and also the dark field signal, there exist a number of different techniques, all of which are envisaged herein in different embodiments. For instance, in some embodiments a relative motion between one of the gratings and the other(s) is required for differential phase extraction (In other embodiments, where the detector can resolve the fringes generated by the grating G1 directly, a relative motion of one of the gratings relative to the detector D can be used as well). The relative motion in either embodiment (that is, grating versus gating or grating versus detector, respectively) can be achieved for instance by "phase stepping", where an actuator is used to laterally move for instance, analyzer grating $G_2$ across different, discrete grating positions and then measure at each grating position the intensity at each pixel PX. "Lateral" motion means herein a motion along z direction (see FIG. 1), that is, a motion in a direction perpendicular to the propagation direction of the wave XB and the "trench" directions of the gratings. The phase-stepping approach has been described by F. Pfeiffer et al in "Phase retrieval and differential phase-contrast imaging with low-brilliance X-ray sources," Nature Phys. Lett. 2, 258-261 (2006).

But that is not to say that phase stepping or this type of phase stepping is the only embodiment, as in other embodiments the motion may be that of the specimen itself or it may be a scanning motion of the X-ray detector (with at least some of the gratings $G_1$ and or $G_2$ mounted therein) which constitutes the required motion. What matters herein, is to capture a series of signals that includes the amount of refraction induced by the presence of the specimen PB in the examination region. In yet other embodiments a multi-focal X-ray source is used and the phase/dark-field signal extraction is realized by switching in sequence from one of the different focal points to another.

In general, no matter which extraction procedure is being used, the intensity I at each pixel will be found to oscillate (in general in a sinusoidal fashion) as a function of the relative position of some X-ray optical element (such as the grating or the detector). For instance referring back to one example of phase stepping, each pixel records a series of different intensities (at the respective pixel) as a function of the different grating positions assumed during lateral motion of the analyzer grating G2.

The oscillating intensity signal I at each pixel px "encodes" amongst the interferometric quantity of main interest herein, that is, the dark field (or small angle scattering) signal and other interferometric quantities such as the overall absorption and the phase shift of the interference pattern. The respective signals (dark field, along with phase and absorption signal) can be extracted in an algorithmic "dark-field retrieval/extraction" (commonly referred to as "phase retrieval" if phase imaging is of interest) operation which is essentially a curve fitting operation for at least all of the above mentioned 3 interferometric quantities. For instance, in one embodiment the phase contrast and dark field signals are recovered as the zero-th and $1^{st}$-order Fourier-components after Fourier-analyzing the respective intensity curve for each pixel PX. See for instance equation (1) and the descriptive text thereto on page 5531 in M Bech et al in "Quantitative X-ray dark-field computed tomography", Phys. Med. Biol. 55 (2010) 5529-5539. As mentioned earlier, the above described grating based interferometric setup is but one embodiment to obtain the dark-field signal. Other, non-grating based setups are also envisaged. Also, the above signal processing to extract the dark-field signal will in general differ from set-up to set-up. By "set-up" (e.g., the here described interferometric set-up) as used herein includes any technical arrangement between detector D and X-ray source that allows an forming an interference pattern at the detector in terms of intensity projection data that can encodes the dark-field scattering signal sought herein. The set-up may include pin-hole/aperture arrangements, crystals arrangements etc. Also, direct dark-field signal arrangements are envisaged herein where there is no additional dark-field-signal extraction/retrieval required from previous, underlying data. In direct imaging, the detector readings themselves form the dark-field signals.

Turning now in more detail to the energy-resolving detector sub-system component, this includes in one embodiment a detector D of the energy-resolving or photon-counting type having a radiation sensitive surface made up from one or more rows of detector pixels PX that are configured to respond by issuing an electrical pulse when impinged on by a photon. A height of said pulse corresponds to the energy of the respective photon. The detector pixels are associated with an "n-bin" photon counting circuitry ER to discriminate between n different energy levels $E_i$ or "bins". In other words, the radiation detected at the detector D (after passage of said radiation through the specimen PB) is analyzed into different photon counts corresponding to the respective energy of impinging photons. The counting circuitry includes in particular a comparator that compares the energy of incoming photons against the predefined set of energy bins $E_i$. More specifically, it is electrical pulses caused by the interaction of the impinging photon with the detector pixels PX that are compared against said energy levels $E_i$.

The previously described phase extraction and phase retrieval operation is carried out for the data in each energy bin to so derive at respective energy resolved dark field projection data L, one for each pixel and each energy level i. The energy resolved dark field data, that is, the collection of all signals for each bin and pixel PX, are then forwarded to a signal processing system SPS.

Figure 4:
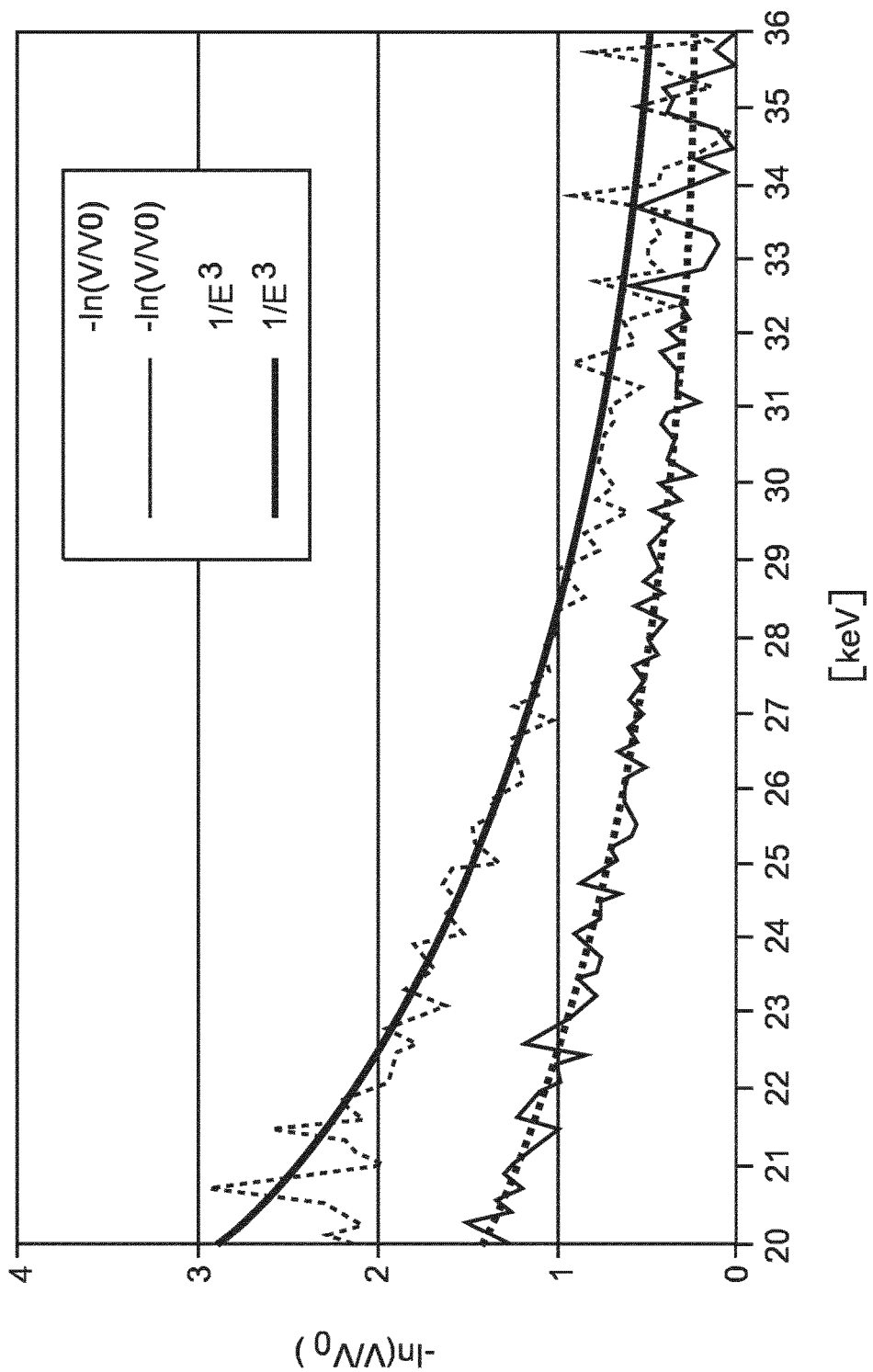
FIG. 4 charts energy dependencies of a dark field signal versus X-ray energy.

The proposed signal processing system SPS operates to improve the signal to noise ratio in dark field imagery by means of energy weighting. Ordinarily, energy weighting has been done only for absorption imagery. It is now proposed herein to do this for dark field imagery also using a new, improved energy model. The model formulates the energy dependence of the dark field signal. Unfortunately, the signal generation process of the dark field signal is fairly complex and hence calls for an involved modelling approach to reflect this complexity. Nevertheless, in some cases, a simple model of isotropic "diffusion" can be applied to describe the dark field signal according as has been reported by elsewhere (see for instance the above referenced Bech et al paper). The diffusion model is:

$$V = V^{(0)} e^{-\int \epsilon(x) dx} \quad (1)$$

which relates the loss of visibility to a so-called linear diffusion coefficient $\epsilon$, with x the path length. FIG. 4 shows experimental results of the energy dependence of the quantity $$l = -\ln \frac{V}{V^{(0)}} = \int \epsilon(x) dx \quad (2)$$

for two foam samples of thicknesses d and 2d, respectively. For each energy, the signal scales well with the sample thickness, which confirms the simple model of signal generation related to a line integral of the diffusion coefficient. Empirically, the energy dependence is found to follow an $E^{-3}$ dependence as evidenced by the fitted curves in FIG. 4 (see the heavy dashed and heavy solid lines). This is a surprising result as the established lore favours an $E^{-2}$ dependency. See for instance [A. Guinier, "X-Ray Diffraction", Dover Publications, Inc, New York, (1994), Chapter 10]. It would then appear that an additional energy dependence component plays in. In a radical departure from existing $E^{-2}$, it is proposed herein to harness this new, empirically established energy dependence for an energy weighting scheme of dark field signals in order to improve the contrast to noise ratio in dark field images assuming the signals were recorded by a spectral detector D.

Figure 2:
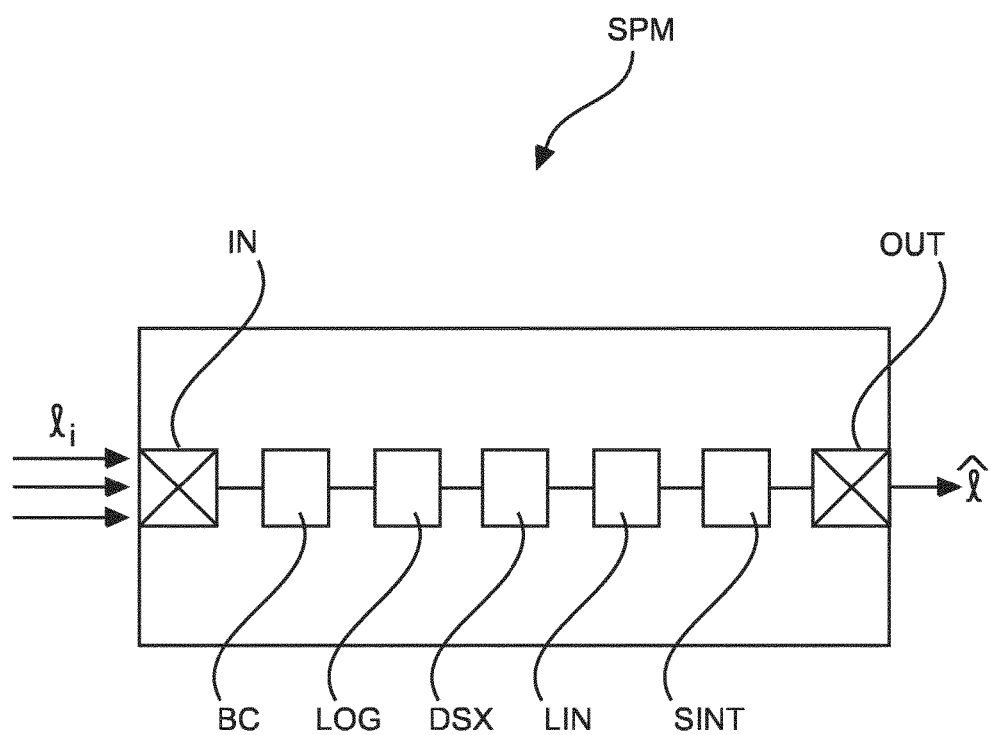
FIG. 2 shows a block diagram of an energy weighting module used in the arrangement of FIG. 1.

FIG. 2 is a block diagram illustrating different components of the signal processing system SPS including an energy weighting module SPM as proposed herein. The module SPM includes an input port IN and an output port OUT. The module reads in at input port IN, energy resolved interferometric projection data recorded at the spectral detector system D. The interferometric projection data is generated after interaction of the X-ray beam (emitted from the X-ray source) with the specimen PB and the interferometric system. The interferometric projection data is then passed on to a dark field signal extractor DSX that operates as briefly described above to extract the dark field signal component from the LOG projection data per energy channel in the context of a suitable phase retrieval curve fitting operation.

As hinted at in eq (2) above, the proposed module SPM is envisaged to operate in a logarithmic domain. In other words, the extracted dark-field signals $V_i$ are passed on to a logarithmic module LOG that operates to convert the signals $V_i$ into their respective logarithms (with respect to any suitable base). In this manner, log-dark-field-signals $l_i$ are formed.

Optionally, there may also be a bias correction module BC configured to apply a bias correction to the received projection data. This is advantageous since the noise level in the individual energy bins might be rather large. Bias correction module can be arranged up-stream or down-stream the logarithmic module LOG.

Optionally, there is a linear transformer LIN that linearly transforms the log-dark-field-signals. Examples for a linear transformer are low- or high pass filter or a backward reconstruction operator such as a filtered backward projection operator (FBP).

The (possibly linearly transformed) log-dark field signals $l_i$ (the same notation "$l_i$" will be used herein whether or not the linear transformation was used) from each energy channel i are then forwarded to a signal integrator SINT. The SINT then operates to implement the energy weighting. In particular, the extracted log-dark field signals are summed over the energy channels and weighted according to the newly proposed energy model. The so integrated and weighted signals (for each detector pixel) are then output at output port OUT to constitute the energy weighted log-dark field signal $\hat{l}$ image. The image can then be forwarded to a screen MT for display after processing with suitable visualizer software or the image can be otherwise stored or processed as required.

Figure 3:
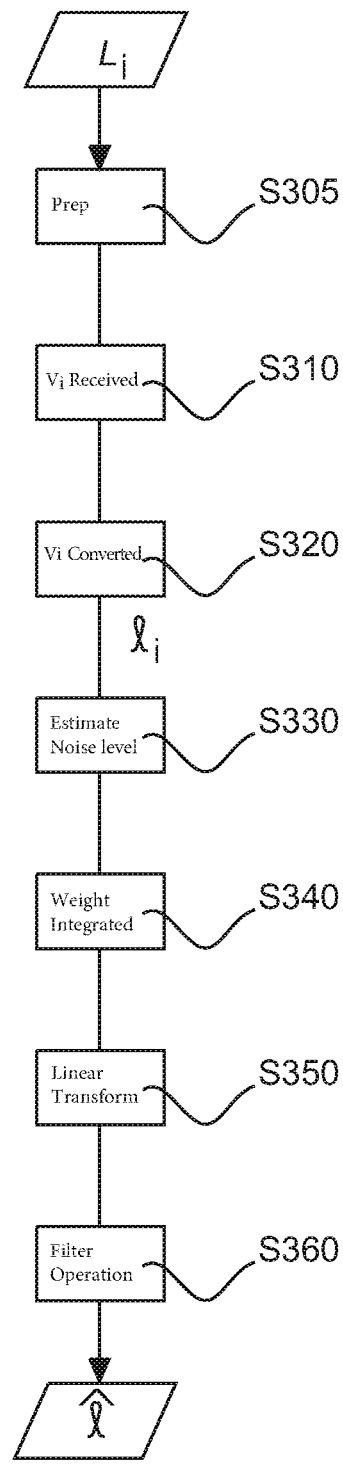
FIG. 3 shows a flowchart of a signal processing method.

The proposed method for energy weighting of log-dark field signals using the improved spectral energy model as proposed herein will now be explained in more detail with reference to flowchart in FIG. 3. The method is explained for a grating-based interferometric set-up which is not to be construed as limiting as other set-ups are likewise envisaged herein as mentioned earlier above.

At step S310, dark field signals $V_i$ are received for or in different energy channels i. The dark field signal may be obtained directly by a suitable detector set-up or may be obtained indirectly via an intermediate extraction processing. For instance, in one exemplary embodiment for this indirect dark-field imaging, a grating-based interferometric setup is used, where, in a preparatory step S305 interferometric projective intensities are received as recorded, in one embodiment, at an n-bin (n≥2) energy resolving detector D for different grating positions. A dark-field signal retrieval or extraction operation is carried out for some (in general for each) energy bin which results then in the dark field signal $V_i$ for the different energy bin i received at step S310.

In step 320, the extracted or directly received dark field signal $V_i$ is converted into a logarithmic representation as log-dark-field signal data $l_i$. Signal processing in the logarithmic domain has the advantage to more conveniently capture and represent the multiplicative nature of the underlying signal generation processes, in particular in respect to dark field signals.

In some embodiments, but not necessarily all embodiments, there is a step S330 to estimate a related noise level a, for the underlying projection data. See for instance Weber et al., "Noise in x-ray grating based phase-contrast imaging", Medical Physics 38(7):4133-4140 (2011) for one method of noise level estimation, where a least square fitting algorithm implemented as a matrix multiplication. See for instance Weber's eq (29) and (32), p 4137 where the variances of the noise behavior are computed. But this is merely one illustrative example and other noise estimation methods are also envisaged herein. In an alternative embodiment, $0^{th}$-order approximation all variances may be taken to be equal and said step S330 is left out entirely.

At step S340, the log-dark field signals $l_i$ are weight integrated to compute a respective energy weighted log-dark field line integral $\hat{l}$ according to:

$$\hat{l} = \frac{1}{\sum_i \tilde{\sigma}_i^{-2}} \sum_i \frac{1}{\tilde{\sigma}_i^2}\left(\frac{E_0^p}{E_i^p} l_i\right) \quad (3)$$

where the term in brackets refers to the log-dark field signal at energy $E_0$ as expected from the measurement at energy $E_i$ by means of a re-scaling. It is then proposed herein to average some or all of the so rescaled values with statistical weights $$\frac{1}{\tilde{\sigma}^2}$$

in order to optimize SNR (signal-to-noise-ratio) of the weighted average. The SNR-optimal weights may be taken as the inverse variances of the rescaled line integrals (as indicated in the notation by tilde ~). This rescaling then implies:

$$\tilde{\sigma}^2 = \left(\frac{E_0^p}{E_i^p}\right)^2 \sigma^2 \quad (3')$$

for an arbitrarily selected reference energy $E_0$, with i indexing the various energy bins/levels.

Applicant has found that for the reciprocal bin energy $E_i^p$, a power law as per $p<-2$ (or, equivalently $1/E_i^p$, $p>2$) yields relatively high signal/noise ratios. In particular, $p=-3$ has proved experimentally to yield good results. Other power values p for the energy law are also envisaged but preferably, $-4 \leq p < -2$.

The above method steps S310-S360 are carried out in parallel or sequentially of each pixel PX or for a user selected plurality of pixels PX.

At step S360, the energy weighted log-dark field image (that is, the collection of energy weighted log-dark signals $\hat{l}$ for all pixels is then output for storage, image processing or display on monitor MT or is otherwise available for use.

The method may also include an optional linear transformation step S350 applied to the projection data or to the (log-) projection data in projection domain. Examples are filter operations, e.g. high- or low pass, etc. In the CT embodiment, said linear filter operation is a reconstruction operation such as a back-projection operation (in particular filtered-back-projection (FBP)). The filter operation S360 is commutative with the energy weighting at step S340. In other words, for CT, energy weighting S340 may be performed as preprocessing as above in 2D projection domain, or as post-processing in 3D image domain, i.e., after filtered back-projection of the log-dark field sinograms (that is, $l_i$ for all projection directions collected during revolution of the scanner's X-ray source around the image specimen PB. In the latter case, that is, if the proposed method is to be applied in the image domain, a proper error propagation method may be used (but not necessarily in all embodiments) in order to propagate the error estimates $\sigma$ (or variances $\sigma^2$) from the projection domain into the image domain. A suitable error propagation method to transform error information from 2D projection domain to 3D image domain is discussed for example in Wunderlich and Noo, "Image covariance and lesion detectability in direct fan-beam x-ray computed tomography", Physics in Medicine and Biology, 53:2471-2493 (2008). See for instance Wunderlich's equations (32), (33), and (37) on page 2479 furnish an algorithm how to FBP-transform the projection domain covariance matrix into one in image domain. The variance in projection domain is first filtered for each view as per eqs (33), (37) and the results so obtained are then back-projected as per eq (32). Other error propagation methods are also envisaged herein.

As can be seen in eq (3), the respective log-dark field signals are doubly weighted in one embodiment, that is, there is weighting based on respective energy terms per bin i which is formed as a ratios between the respective energy level and an arbitrary design energy $E_0$ and there is also weighting by the reciprocals of the estimated noise level as per the statistical variances computed in step S330 for each bin i. The rationale can be understood from the underlying model $l(E)=(E/E_0)^p l(E_0)$ and the re-scaling as per eq (3') above. This allows relating the measured data to the "reference" or designing energy $E_0$.

Optionally, there may also be a bias correction step to apply a bias to the received projection data. This is advantageous since the noise level in the individual energy bins might be rather large. If left uncorrected these noise levels may lead to the undesirable effect of bias, i.e., a systematic error in the estimated dark-field signal.] Bias correction can be achieved for instance as explained in references Gudbarjartsson et al, "The Rician Distribution for Noisy MRI Data", MRM 34:910-914 (1995) or Henkelman, "Measurement of signal intensities in the presence of noise in MR images", Medical Physics 12:232-233 (1985), Erratum in 13:544 (1986). The above described power law energy model $E^p$ ($p<-2$) as used for the weighting as per eq (3) is a useful approximation derivable from a more refined signal model discovered by Applicant, namely:

$$-\ln\left(\frac{V}{V^{(0)}}\right) = \frac{a}{E^2} * \left(1 - \exp\left(-b\left(\frac{E0}{E}\right)^2\right)\right) \quad (4)$$

With $V, V^{(0)}$ indicating the respective interferometric visibilities obtained from the phase retrieval as the zero-th and first order Fourier component.

The simplified energy model $E^p$ ($p<-3$) as used in energy-weighting equation can be obtained by taking the limits for large $b \gg 1$ or $b \ll 1$. For $b \ll 1$, the exponential function component exp can be developed into a Taylor series expression and we find an $E^{-4}$ power law energy dependency. For $b \gg 1$, exp tends to zero and we have the $E^{-2}$ dependency. Constant b in eq (4) has been found to relate to the average particle size or microstructures in the sample that are thought to cause the small angle scattering. In other words energy weighting based on the $E^{-3}$ energy law may thus be preferable where the average microstructure size is usually large whereas as the $E^{-4}$ approximation may be called for when the microstructure size is rather small. The more detailed energy model eq (4) may thus be useful as a "middle-ground" approximation. However the simplified model has been found in most experimental scenarios to yield good results as evidenced by the charts in FIG. 4. Microstructure particle size parameter b is either known a-priori or is used as an additional parameter when curve fitting the data. Parameter a in eq (5) can usually be taken as a=1 or indeed as any value because this parameter cancels out when forming the ratios with design energy $E_0$ in energy weighting or integrating step S340.

Using the more refined energy law as per eq (4), the energy weighted log-dark field signal can be computed as:

$$\hat{t} = \frac{1}{\sum_i \hat{\sigma}_i^{-2}} \sum_i \frac{1}{\hat{\sigma}_i^2} \left[ \frac{a}{E_i^2} \left( 1 - \exp\left(-b\left(\frac{E_0}{E_i}\right)^2\right) \right) \right]^{-1} t_i \quad (5)$$

where now the more simplified approximative energy law $$\frac{E_0^p}{E_i^p}$$

in the energy weighting formula of eq (3) is replaced by eq (4). The rescaling counterpart to eq (3') can now be written as:

$$\hat{\sigma}^2 = \left[ \frac{a}{E_i^2} \left( 1 - \exp\left(-b\left(\frac{E_0}{E_i}\right)^2\right) \right) \right]^{-2} \sigma^2 \quad (5')$$

As can be seen, in the more refined approximation as per (4), it is now the bin energy terms $E_i$ themselves that appear in the respective exponents of the exp expression.

Mathematical equivalents or approximative expressions of the above described energy models for energy weighting purposes are also envisaged herein and encompassed by appended claims.

In one embodiment, the system includes suitable user input means such as a graphical user interface or keyboard to adjust particle size parameter b. The model can thus be adjusted to different by the user to the expected structures or the user can generate different energy weighted dark-field images by tweaking b.

The energy dependence (that is, parameter p) as used above may either be known a priori or may itself be derived from the given projection data set V by for instance a least-square-fitting to a power law in the form $E_i^{-p}$.

Although the above has been explained with reference to an X-ray imaging system IM having an energy resolving detector D, it will be appreciated that the above described method and system is of equal application to X-ray imaging system IM where the detector D is of the energy integrating type. In this embodiment, the X-ray source XR operable by switching at different X-ray tube voltages which then define the different energy levels i. The energy resolving is achieved by acquiring different sets of projection data at multiple exposures with different tube voltages.

One or more components (such as module SPM) of the signal processing system SPS as proposed herein may be run or implemented as a software module(s) in a suitably configured data processing or computing unit such as a work station WS associated with the imager IM. Alternatively the signal processing system SPS may be programmed in a suitable programming language such as C++ or C. Alternatively, the signal processing system SPS or at least some of its components may be hardwired as a standalone computer chip or may be arranged as a dedicated FPGA. Other implementational realizations are also envisaged herein.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus.

The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A signal processing apparatus, comprising:
a memory that stores a plurality of instructions; and
a processor coupled to the memory and configured to execute the plurality of instructions to:
receive dark-field signal data for different energy channels, the dark-field signal data corresponding to signals detected, in different energy channels, after exposure to X-ray radiation from an X-ray source;
logarithmize the dark-field signal data to obtain log-dark-field signal data;
transform the log-dark-field signal data via linear transformation when the plurality of instructions include performing optional linear transformation;
integrate the linearly transformed log-dark-field signal data or the log-dark-field signal data of at least two energy channels into an energy weighted log-dark-field signal by using energy weights corresponding to the at least two energy channels, and
output said energy weighted log-dark-field signal.

2. The signal processing apparatus as per claim 1, wherein the energy weights include a respective energy term that can be expressed in the form $E^p$ with $p<-2$.

3. The signal processing apparatus as per claim 2, wherein $-4 \leq p < -2$.

4. The signal processing apparatus as per claim 1, wherein the detected signals correspond to projection data, and the processor is further configured to execute the plurality of instructions to extract, for at least two energy channels, from intensity data, the respective dark-field signal data, the intensity data being derived from the projection data.

5. The signal processing apparatus as per claim 1, wherein the energy weights include respective energy terms, at least one of the energy terms having an energy value as an exponent.

6. The signal processing apparatus as per claim 5, wherein the energy weights include respective energy terms of the form $$\frac{a}{E_i^2} * \left(1 - \exp\left(-b\left(\frac{E_0}{E_i^2}\right)^2\right)\right),$$

wherein
a is an arbitrary constant,
b is a constant that relates to an internal structure of an imaged object,
$E_0$ is a design energy, and
$E_i$ are energy levels for the different energy channels i.

7. The signal processing apparatus as per claim 1, wherein the optional linear transformation is performed by any one of:
(i) a high pass filter or a low-pass filter or
(ii) a backward-projection operator.

8. The signal processing apparatus as per claim 1, wherein the processor is further configured to execute the plurality of instructions to apply a bias correction to dark field projection data corresponding to the received dark-field signal data.

9. An imaging system, comprising:
a detector;
an X-ray source; and
a signal processing apparatus including:
a memory that stores a plurality of instructions; and
a processor coupled to the memory and configured to execute the plurality of instructions to:
receive dark-field signal data for different energy channels, the dark-field signal data corresponding to signals detected, in different energy channels, at the detector after exposure to X-ray radiation from the X-ray source;
logarithmize the dark-field signal data to obtain log-dark-field signal data;
transform the log-dark-field signal data via linear transformation when the plurality of instructions include performing optional linear transformation;
integrate the linearly transformed log-dark-field signal data or the log-dark-field signal data of at least two energy channels into an energy weighted log-dark-field signal by using energy weights corresponding to the at least two energy channels, and
output said energy weighted log-dark-field signal.

10. The imaging system as per claim 9, wherein the imaging system is a computed tomography (CT) scanner or a planar projection X-ray imager.

11. The imaging system as per claim 9, wherein
i) the detector is an energy resolving detector, and the different energy channels correspond to different energy values of the energy resolving detector; or
ii) the detector is an energy integrating detector, and the different energy channels correspond to detector readings for X-ray exposures by the X-ray source at different voltage levels.

12. A signal processing method, comprising:
receiving, for different energy channels, respective dark-field signal data, the dark-field signal data corresponding to signals detected, in the different energy channels, after exposure to X-ray radiation from an X-ray source;
logarithmizing the dark-field signal data to obtain log-dark-field signal data;
optionally, linearly transforming the log-dark-field signal data;
integrating the log-dark-field signal data or the linearly transformed log-dark-field signal data of at least two energy channels into an energy weighted log-dark-field signal by using energy weights corresponding to the at least two energy channels; and
outputting said energy weighted log-dark-field signal.

13. The signal processing method as per claim 12, wherein the energy weights include a respective energy term that can be expressed in the form $E^p$ with $p<-2$.

14. A non-transitory computer-readable medium storing computer-readable instructions, which, when being executed by a processor, cause the processor to perform a signal processing method comprising:
receiving, for different energy channels, respective dark-field signal data, the dark-field signal data corresponding to signals detected, in the different energy channels, after exposure to X-ray radiation from an X-ray source;
logarithmizing the dark-field signal data to obtain log-dark-field signal data;
optionally, linearly transforming the log-dark-field signal data;

integrating the log-dark-field signal data or the linearly transformed log-dark-field signal data of at least two energy channels into an energy weighted log-dark-field signal by using energy weights corresponding to the at least two energy channels; and outputting said energy weighted log-dark-field signal.

* * * * *